United States Patent [19]

Villax et al.

[11] Patent Number: 5,026,693
[45] Date of Patent: Jun. 25, 1991

[54] 9-α-FLUORO- OR CHLORO-CORTICOSTEROID ESTERS AND A PROCESS FOR THEIR PREPARATION

[75] Inventors: Ivan Villax, Lisbon; William Heggie, Barreiro; Philip R. Page, Parede, all of Portugal

[73] Assignee: Hovione Inter Ltd., Switzerland

[21] Appl. No.: 527,718

[22] Filed: May 21, 1990

Related U.S. Application Data

[63] Continuation of Ser. No. 758,289, Jul. 24, 1985, abandoned.

[30] Foreign Application Priority Data

Jul. 25, 1984 [PT] Portugal ................... 78973

[51] Int. Cl.$^5$ .................. A61K 31/56; C07J 9/00; C07J 7/00
[52] U.S. Cl. .................... 514/180; 552/540; 552/548; 552/554; 552/569; 552/589; 552/590; 552/596; 552/598; 552/622; 552/650
[58] Field of Search ........... 260/239.55 R, 397.45; 514/180; 552/540, 548, 554, 569, 589, 590, 596, 598, 622, 650

[56] References Cited

U.S. PATENT DOCUMENTS 3,312,590  4/1967  Elks et al. ............ 514/180
4,555,507  11/1985  Annen et al. .......... 260/239.55 R

FOREIGN PATENT DOCUMENTS 1443957  3/1984  Fed. Rep. of Germany .

*Primary Examiner*—Stanley J. Friedman
*Assistant Examiner*—Diane Gardner
*Attorney, Agent, or Firm*—Ostrolenk, Faber, Gerb & Soffen

[57] ABSTRACT

Novel esters of 9α-fluoro- and chloro-corticosteroids of the formula

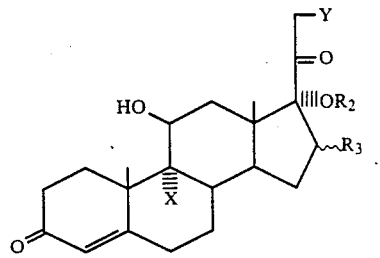

wherein Y is chlorine or $OR_1$, $R_1$ and $R_2$ represent an acyl group of 2-6 carbon atoms or a benzoyl group and where $R_1$ and $R_2$ can be the same or different in the same molecule, $R_3$ is methyl or fluorine in either the α- or β- orientation, X is chlorine or fluorine, and the $C_1$ — $C_2$ bond can be saturated or not, especially those compounds of the formula

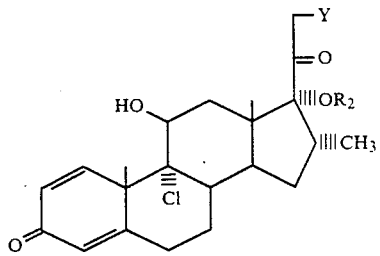

wherein Y and $R_2$ have the significance given above, are prepared by reacting the respective 9β,11β-epoxy compounds with hydrogen fluoride or chloride.

24 Claims, No Drawings

NOVEL 9-α-FLUORO- OR CHLORO-CORTICOSTEROID ESTERS AND A PROCESS FOR THEIR PREPARATION

This is a continuation of application Ser. No. 06/758,289 filed on July 24, 1985 now abandoned.

Corticosteroids have been long known for their anti-inflammatory activity. It has been similarly known that the anti-inflammatory activity can be considerably enhanced by the introduction of ester functions at the 17- and 21- positions. The present invention concerns a process for the preparation of 17-monoacylates and 17,21-diacylates of corticosteroids and additionally the novel products that can be so prepared using the process.

The preparation of such esterified corticosteroids according to the prior art can be split into three major groups.

The first is by esterification without protection at the 11-position. This is exemplified in British Pat. No. 737,291. This process suffers from a lack of specificity for the required 17,21-diacylated product, when the 11-substituent is a hydroxyl group.

The second general method is the use of 11- hydroxyl protection, prior to esterification. Protection by a trihaloacetyl group, the trimethylsilyl ether group, the tetrahydropyran-2'-yl group, and the nitrate ester have all been proposed, variously in British Pat. Nos. 1,097,165, 1,227,992 and 1,082,573 and U.S. Pat. No. 4,024,131. The following esterification can be accomplished by a wide variety of methods, with the best being described in European patent specification No. 72,200. All of these processes are somewhat lengthy due to the necessity of introducing and then removing the 11- protecting group.

The final general method is by the acid hydrolysis of 17,21-orthoesters, which can be prepared without 11-protection, followed by 21-acylation. However, the necessary trialkyl orthoester reagents are difficult to prepare and usually not commercially available, added to the fact that the acid hydrolysis often gives mixtures of the 17-monoester and 21-monoester, plus variable amounts of the 17,21-dihydroxy starting material. This method is described in British Pat. Nos. 996,079, 996,080, 1,043,347, 1,047,518 and 1,047,519.

According to the present invention, there is provided a process for the preparation of 17,21-diacylates of 9α-fluoro- or chloro-17,21-dihydroxycorticosteroids and of 17-acylates of 9α-fluoro- or chloro-17-hydroxycorticosteroids of the formula

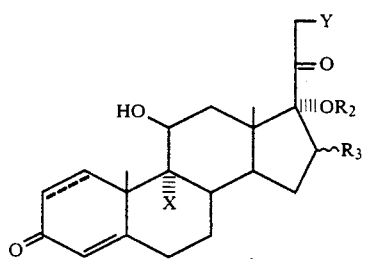

(I)

wherein Y is chlorine or $OR_1$, $R_1$ and $R_2$ represent an acyl group of 2 to 6 carbon atoms or a benzoyl group and where $R_1$ and $R_2$ can be the same or different in the same molecule, $R_3$ is methyl or fluorine in either the α- or β- orientation, X is chlorine or fluorine, and the $C_1 = C_2$ bond can be saturated or not, characterised by the fact that a compound of the formula

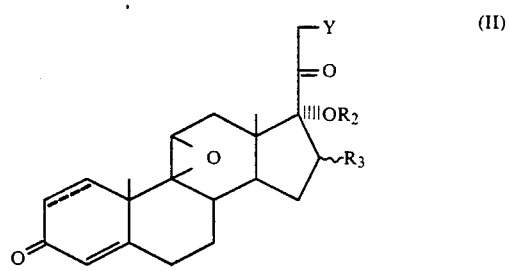

(II)

wherein Y, $R_2$, $R_3$ and $C_1 = C_2$ have the significance given above, is reacted with hydrogen chloride or fluoride.

Whilst the process of chlorination or fluorination of a 9,11-epoxide per se is known in the literature, for example in U.S. Pat. No. 4,154,748 and in British Pat. No. 1,296,458, we have now discovered that the process can be applied to a starting material of formula II, allowing the preparation of steroidal esters, many of which have not been described in the prior art and which have significant anti-inflammatory activity when compared with other known corticosteroid esters.

The corticosteroid esters of the formula

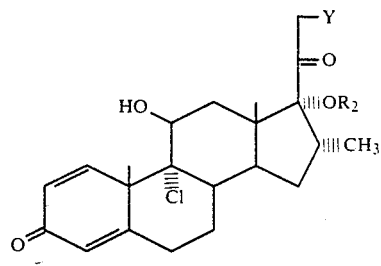

wherein Y and $R_2$ are as defined above, can be made by the process of the present invention. All but four of these are novel and these novel compounds form a further inventive feature of the present invention. Those known are where Y is chlorine and $R_2$ is propionyl; Y and $R_2$ are propionyl; Y is acetyl and $R_2$ is propionyl; and Y is acetyl and $R_2$ is valeryl.

The starting materials can be prepared according to the known processes, such as diesterification of

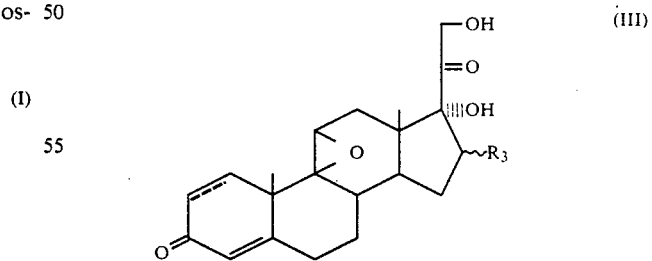

(III)

when symmetrical diesters are required. When non-symmetrical 17,21-diesters are required, the 21-acylate of the compound of formula III is used as starting material. Alternatively, the 17,21-orthoester can be prepared, followed by acid hydrolysis to give the 17-monoester, which is then acylated at the 21- position. By this method, both symmetrical and non-symmetrical 17,21-diesters are available.

Alternatively, the compound

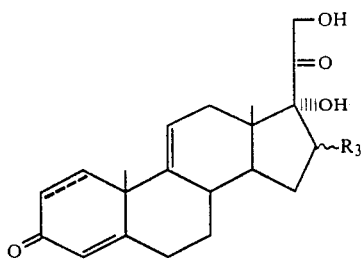

(IV)

is diacylated by either of the methods given above, then reacted with a reagent capable of producing hypobromous acid in situ (such as N-bromoacetamide in the presence of perchloric acid) to give the 9α-bromo-11β-hydroxyl compound, followed by epoxidation, for example using potassium acetate.

In order to prepare a compound of formula II, in which Y is chlorine, a compound of formula III can be transformed into the 21-mesylate and then reacted with an alkali metal chloride, such as lithium chloride, followed by 17-acylation. Alternatively, the 17-ester function is introduced via the 17,21-orthoester, prior to the introduction of the 21-chloro- group.

The starting material is dissolved in an organic solvent, or a mixture of such. The solvents useful in the present invention comprise dimethylformamide, tetrahydrofuran, dioxan, ketones such as acetone, halogenated hydrocarbons such as chloroform, and lower alcohols with 1 to 3 carbon atoms. The solution is then cooled to between −60° C. and 0° C., preferably between −30° C. and −5° C.

The hydrogen fluoride or hydrogen chloride is dissolved in an organic solvent, which can be the same or different from that used in the dissolution of the steroidal starting material, or in water. The concentration is preferably between about 35% and about 75% weight/weight.

After cooling, the acid solution is added slowly to the steroid solution ensuring that the temperature does not rise above the selected reaction temperature. After the addition, the reaction mixture is stirred at a controlled temperature of between −60° C. and +20° C., preferably between −20° C. and +10° C.

After completion of the reaction, the reaction mixture is treated with a cold non-solvent, which is miscible with the reaction mixture and in which the required product is insoluble. A preferred non-solvent is a mixture of water and ice. Additionally, the non-solvent can be mixed with a base prior to addition to the reaction mixture. The group of useful bases comprises sodium carbonate, sodium bicarbonate, ammonia solution and an organic amine, such as triethylamine. The quantity of base is calculated such that the pH of the mixture after precipitation is between 3 and 7. Above pH 7, there would be present free base which could cause hydrolysis or solvolysis of the 17- and/or 21-ester functions.

Alternatively, the base can be added after the precipitation of the required product.

In either case, the temperature of the precipitation should be controlled so as not to allow it to rise significantly during the neutralisation of the acid reagent. Preferably it should be kept below or about 0° C. during the actual precipitation. The product can then be recovered by conventional means, such as filtration, followed by drying.

Thus, the compounds of formula I can be prepared in good yield and purity, with the advantage of not causing hydrolysis of the ester functions.

The novel compounds of the present invention were shown to have surprising anti-inflammatory activity. Thus, in the rat's foot oedema test it was shown that most of the compounds were as good as or better than the standard of betamethasone 17-valerate. More concretely, the 17-propionate 21-butyrate and the 17,21-dibutyrate of 9α-chloro-11β,17α,21-trihydroxy-16α-methylpregna-1,4-diene-3,20-dione were several times more active than the standard. Similarly, in the vasoconstriction test described originally by A. W. McKenzie and R. B. Stoughton in Arch. Derm. 86, 608–610, (1962), several of the novel compounds were shown to be more active than the betamethasone 17-valerate standard, especially the aforementioned 9α-chloro-11β,17α,21-trihydroxy-16α-methylpregna-1,4-diene-3,20-dione 17-propionate 21-butyrate.

Certain of the compounds which can be made by the process of the present invention are novel per se and form a further aspect of the present invention. These include the following 17,21-diacylates of 9α-chloro-11β,17α,21-trihydroxy-16α-methylpregna-1,4-diene-3,20-dione:

17,21-diacetate
17-acetate 21-propionate
17-acetate 21-butyrate
17-acetate 21-valerate
17-acetate 21-benzoate
17-propionate 21-butyrate
17-propionate 21-valerate
17-propionate 21-benzoate
17-butyrate 21-acetate
17-butyrate 21-propionate
17,21-dibutyrate
17-butyrate 21-valerate
17-butyrate 21-benzoate
17-valerate 21-propionate
17-valerate 21-butyrate
17,21-divalerate
17-valerate 21-benzoate and
9α-fluoro-11,17α,21-trihydroxy-16-methylpregna-1,4-diene-3,20-dione 17-propionate 21-butyrate
9α-fluoro-11,17α,21-trihydroxy-16-methylpregna-1,4-diene-3,20-dione 17-valerate 21butyrate The products of the present invention when mixed with pharmaceutically acceptable excipients and diluents, well known to those skilled in the art, are active in locally applied topical formulations. Thus, the present invention includes pharmaceutical compositions which comprise a novel compound of the invention, and an inert pharmaceutically acceptable carrier therefor.

Typical of the formulations are creams, lotions, ointments, eye-drops and oral inhalation sprays. The content of the active principle depends on the actual formulation, but is generally between 0.001% w/w and 0.5% w/w, more preferably between 0.01% and 0.25% w/w.

The formulations prepared with the products of the present invention can be used in the topical treatment of corticosteroid-responsive dermatoses, which may include psoriasis, eczemas, neurodermatitis, seborrheic dermatitis, contact dermatitis, atopic dermatitis and intertrigo.

The following examples serve to illustrate the present invention, without in any way limiting the scope thereof.

All U.V. values quoted are in terms of $E_{1\ cm}^{1\%}$.

EXAMPLE 1

Preparation of 9α-fluoro-11β,17α,21-trihydroxy-16α-methylpregna-1,4-diene-3,20-dione 17,21-dipropionate Method A:

A solution of hydrogen fluoride in dimethylformamide (66.5%; 70 ml) was cooled to −13° C. in an ice salt bath. 9β,11β-Epoxy-17α,21-dihydroxy-16α-methylpregna-1,4-diene-3,20-dione 17,21-dipropionate (10.0 g; 20.6 mmoles) was added during 15 minutes, with constant stirring of the reaction mixture, whence the temperature rose to −10° C. Stirring was continued for 3 hours and 40 minutes with the temperature being maintained at −10° C. ±2° C. The reaction mixture was then precipitated in ice/water (262.5 ml) containing ammonia solution (32%; 55 ml). The pH was then adjusted to 6–7 using ammonia solution (32%), the solid filtered, washed abundantly with water and dried at 50° C., thus giving a yield of 10.1 g (97% of theoretical) of 9α-fluoro-11β,17α,21-trihydroxy-16α-methylpregna-1,4-diene-3,20-dione 17,21-dipropionate.

Recrystallisation from methanol gave the analytical sample:
m.p.=203°–204° C.
$\{\alpha\}_D^{25} = 31.2°$ (dioxan).
U.V.=311 at 238–240 nm (methanol).

Method B:

A solution of hydrogen fluoride in dimethylformamide (66.5%; 37.5 ml) was cooled to −10° C. in an ice salt bath and acetone (12.5 ml) was added. 9β,11β-Epoxy-17α,21-dihydroxy-16α-methylpregna-1,4-diene-3,20-dione 17,21-dipropionate (5.0 g; 10.3 mmoles) was added in such a way as to maintain the temperature at 5° C.±2° C. under constant stirring. This temperature was maintained for 1 hour and 30 minutes, after which the reaction mixture was precipitated in ice/water (131.25 ml) containing ammonia solution (32%; 29.5 ml). The pH was then adjusted to 6–7 using ammonia solution (32%), the product filtered, washed abundantly with water and dried at 50° C., giving a yield of 5.1 g (98% of theoretical) of 9α-fluoro-11β,17α,21-trihydroxy-16α-methylpregna-1,4-diene-3,20-dione 17,21-dipropionate. Recrystallisation from methanol gave the analytical sample:
m.p.=202°–205° C.
$\{\alpha\}_D^{25} = +31.6°$ (dioxan).
U.V.=318 at 242–3 nm (methanol).

EXAMPLE 2

Preparation of 9α-fluoro-11β,17α,21-trihydroxy-16α-methylpregna-1,4-diene-3,20-dione 17-propionate 21-acetate A solution of hydrogen fluoride in dimethylformamide (66.5%; 0.75 ml) was cooled to −5° C. and acetone (0.25 ml) was added. 9β,11β-Epoxy-17α,21-dihydroxy-16α-methylpregna-1,4-diene-3,20-dione 17-propionate 21-acetate (100 mg; 0.21 mmoles) was added with stirring and maintaining the temperature between 0° C. and 5° C. After 1 hour and 30 minutes, the reaction mixture was precipitated in ice/water (5 ml) containing ammonia solution (25%; 0.75 ml) and the pH of the mixture then adjusted to 6–7 using ammonia (25%). The solid was filtered, washed abundantly with water and dried at 35° C., to yield 72.8 mg. The analytical sample was obtained by crystallisation from methanol:
m.p.=194°–5° C.
U.V.=312 at 238–9 nm (methanol).

EXAMPLE 3

The following 17,21-diacylates of 9α-fluoro-11β,17α,21-trihydroxy-16α-methylpregna-1,4-diene-3,20-dione were prepared using the method of Example 2:

17-butyrate 21-acetate
m.p.=169°–172° C.
17-propionate 21-butyrate
m.p.=200°–1° C.
17-valerate 21-acetate
m.p.=165°–6° C.
U.V.=291 at 238–9 nm (methanol).
17,21-divalerate
m.p.=196°–7° C.
17-valerate 21-butyrate
m.p.=155°–6° C.
U.V.=278 at 238 nm (methanol)

EXAMPLE 4

Preparation of 9α-fluoro-11β,17α,21-trihydroxy-16α-methylpregna-1,4-diene-3,20-dione 17-valerate 21-propionate A solution of hydrogen fluoride in dimethylformamide (66.5%; 3 ml) was cooled to −5° C. and dioxan (1 ml) was added, followed by 9β,11β-epoxy-17α,21-dihydroxy-16α-methylpregna-1,4-diene-3,20-dione 17-valerate 21-propionate (0.4 g; 0.78 mmoles) with constant stirring, while the temperature was maintained at 0° C.. After 1 hour and 30 minutes, the reaction mixture was precipitated in ice/water (20 ml) containing ammonia solution (25%; 3 ml). The resulting mixture was neutralised, the solid filtered, washed abundantly with water and dried at 35° C. The yield of 9α-fluoro-11β,17α,21-trihydroxy-16α-methylpregna-1,4-diene-3,20-dione 17-valerate 21-propionate was 0.38 g (91.4% of theoretical).

The analytical sample had the following analysis:
m.p.=146°–8° C.
U.V.=299 at 239 nm (methanol).

EXAMPLE 5

Preparation of 9α-chloro-11β,17α,21-trihydroxy-16α-methylpregna-1,4-diene-3,20-dione 17-propionate 21-benzoate 9β,11β-Epoxy-17α,21-dihydroxy-16α-methylpregna-1,4-diene-3,20-dione 17-propionate 21-benzoate (400 mg; 0.785 mmoles) was added slowly with stirring to a pre-cooled solution of hydrogen chloride in dimethylformamide (50%; 4 ml) maintained at −5° C.. The reaction mixture was stirred for 2 hours and 30 minutes at a temperature of −5° C. to 0° C., and then precipitated in ice/water (40 ml) containing ammonia solution (25%; 3 ml). The resulting mixture was then neutralised, the solid filtered, washed with water and dried at 35° C. The yield was 410 mg (96% of theoretical).
m.p.=245°–6° C.
$\{\alpha\}_D^{25} = +61.5°$ (dioxan)
U.V.=468 at 234 nm (methanol)

EXAMPLE 6

The following 17,21-diacylates of 9α-chloro-11β,17α,21-trihydroxy-16α-methylpregna-1,4-diene-3,20-dione were prepared using the method of Example 5:

17,21-diacetate
  m.p.=240°-2° C.
  $\{\alpha\}_D^{25}=+55.8°$ (dioxan)
  U.V.=312 at 240 nm (methanol)
17-acetate 21-propionate
  m.p.=222°-3° C.
  $\{\alpha\}_D^{25}=+55.5°$ (dioxan)
  U.V.=303 at 239-240 nm (methanol)
17-acetate 21-butyrate
  m.p.=200°-1° C.
  $\{\alpha\}_D^{25}=+53.6°$ (dioxan)
  U.V.=298 at 240 nm (methanol)
17-acetate 21-valerate
  m.p.=215°-6° C.
  $\{\alpha\}_D^{25}=+53.9°$ (dioxan)
  U.V.=291 at 239-240 nm (methanol)
17-acetate 21-benzoate
  m.p.=243°-4° C. (decomp.)
  $\{\alpha\}_D^{25}=+61.7°$ (dioxan)
  U.V.=483 at 233 nm (methanol)
17-propionate 21-butyrate
  m.p.=231°-2° C.
  $\{\alpha\}_D^{25}=+54.2°$ (dioxan)
  U.V.=288 at 240 nm (methanol)
17-propionate 21-valerate
  m.p.=227°-8° C.
  $\{\alpha\}_D^{25}=+55.0°$ (dioxan)
  U.V.=280 at 238-9 nm (methanol)
17-propionate 21-benzoate
  m.p.=245°-6° C. (decomp.)
  $\{\alpha\}_D^{25}=+61.5°$ (dioxan)
  U.V.=468 at 234 nm (methanol)
17-butyrate 21-acetate
  m.p.=212°-3° C.
  $\{\alpha\}_D^{25}=+52.5°$ (dioxan)
  U.V.=294 at 239-240 nm (methanol)
17-butyrate 21-propionate
  m.p.=220°-1° C.
  $\{\alpha\}_D^{25}=+55.5°$ (dioxan)
  U.V.=287 at 239-240 nm (methanol)
17,21-dibutyrate
  m.p.=219°-220° C.
  $\{\alpha\}_D^{25}=+53.3°$ (dioxan)
  U.V.=281 at 239-240 nm (methanol)
17-butyrate 21-valerate
  m.p.=193°-4° C.
  $\{\alpha\}_D^{25}=+54.4°$ (dioxan)
  U.V.=274 at 238-9 nm (methanol)
17-butyrate 21-benzoate
  m.p.=219°-220° C.
  $\{\alpha\}_D^{25}=+59.0°$ (dioxan)
  U.V.=456 at 233-4 nm (methanol)
17-valerate 21-acetate
  m.p.=201°-2° C.
  $\{\alpha\}_D^{25}=+50.8°$ (dioxan)
  U.V.=283 at 239-240 nm (methanol)
17-valerate 21-propionate
  m.p.=181°-2° C.
  $\{\alpha\}_D^{25}=+54.3°$ (dioxan)
  U.V.=282 at 239 nm (methanol)
17-valerate 21-butyrate
  m.p.=199°-200° C.
  $\{\alpha\}_D^{25}=+51.4°$ (dioxan)
  U.V.=275 at 240 nm (methanol)
17,21-divalerate
  m.p.=165°-6° C.
  $\{\alpha\}_D^{25}=+52.2°$ (dioxan)
  U.V.=266 at 239-240 nm (methanol)
17-valerate 21-benzoate
  m.p.=187°-190° C.
  $\{\alpha\}_D^{25}=+55.7°$ (dioxan)
  U.V.=445 at 233 nm (methanol)

EXAMPLE 7

Preparation of 21-chloro-9α-fluoro-11β, 17α-dihydroxy-16β-methylpregna-1,4-diene-3,20-dione 17-propionate The conditions of Example 1, Method A, were repeated using as starting material 21-chloro-9β,11β-epoxy-17α, hydroxy-16β-methylpregna-1,4-diene-3,20-dione 17-propionate. The product so obtained had the following analytical values:
  m.p.=197°-8° C.
  U.V.=343 at 238-9 nm (methanol).

EXAMPLE 8

Preparation of 9α-chloro-11β,17α,21-trihydroxy-16β-methylpregna-1,4-diene-3,20-dione 17,21-dipropionate The conditions of Example 5 were repeated using 9β,11β-epoxy-17α,21-dihydroxy-16β-methylpregna-1,4-diene-3,20-dione 17,21-dipropionate as starting material. The product so obtained had the following analytical values:
  m.p.=211°-3° C.
  U.V.=306 at 239 nm (methanol).

We claim:
1. A process for the preparation of 17,21-diacylates of 9α-fluoro- or chloro-17,21-dihydroxy-corticosteroids and of 17-acylates of 9α-fluoro- or chloro-17-hydroxy-corticosteroids of the formula

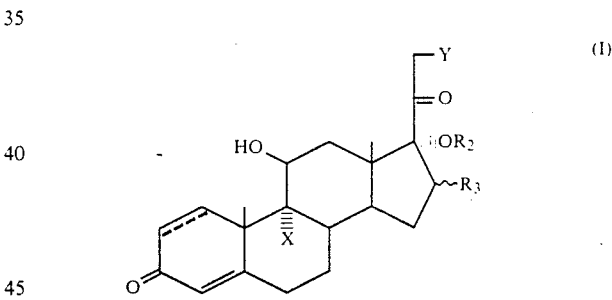

wherein Y is chlorine or OR$_1$, R$_1$ and R$_2$ represent an acyl group of 2 to 6 carbon atoms or a benzoyl group and where R$_1$ and R$_2$ can be the same or different in the same molecule, R$_3$ is methyl or fluorine in either the α- or β- orientation, X is chlorine or fluorine, and the C$_1$===C$_2$ bond can be saturated or not, characterised by the fact that a compound of the formula

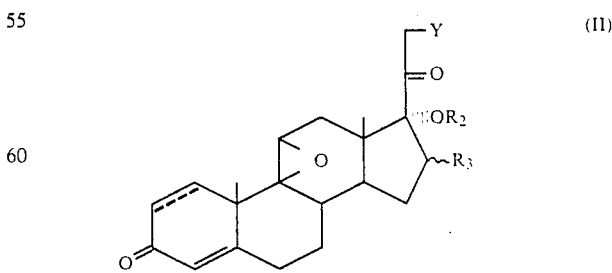

wherein Y, R$_2$ and R$_3$ and C$_1$===C$_2$ have the significance given above, is reacted with hydrogen chloride or fluoride.

2. A process according to claim 1, characterised by the fact that excess hydrogen chloride or fluoride is mixed with an organic solvent or with water, and the reaction temperature is controlled between −60° C. and +20° C.

3. A process according to claim 2, characterised by the fact that the reaction temperature is controlled between −20° C. and +10° C.

4. A process according to claim 2, characterised by the fact that the final product of the reaction is isolated by mixture with a non-solvent at a temperature about 0° C. and the final pH of the reaction mixture is between 3 and 7.

5. A process according to claim 4, characterised by the fact that the non-solvent is water and ice, and the pH is adjusted with sodium carbonate or bicarbonate, ammonia solution or an organic amine.

6. A process according to claim 4, characterised by the fact that the compound of formula II is reacted with hydrogen chloride.

7. A process according to claim 1, characterised by the fact that the final product of the reaction is isolated by mixture with a non-solvent at a temperature about 0° C. and the final pH of the reaction mixture is between 3 and 7.

8. A process according to claim 7, characterised by the fact that the non-solvent is water and ice, and the pH is adjusted with sodium carbonate or bicarbonate, ammonia solution or an organic amine.

9. A process according to claim 8, characterised by the fact that the compound of formula II is reacted with hydrogen chloride.

10. A process according to claim 11, characterised by the fact that the compound of formula II is reacted with hydrogen chloride.

11. A compound of the formula

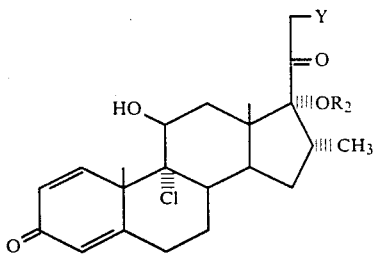

wherein Y is chlorine or $OR_1$, $R_1$ and $R_2$ represent an acyl group of 2 to 6 carbon atoms or a benzoyl group and where $R_1$ and $R_2$ can be the same or different in the same molecule, with the exclusion from the above of the compounds where Y is chlorine and $R_2$ is propionyl; Y and $R_2$ are propionyl; Y is acetyl and $R_2$ is propionyl; and Y is acetyl and $R_2$ is valeryl.

12. A compound selected from the group consisting of

9α-chloro-11β,17α,21-trihydroxy-16α-methylpregna-1,4-diene-3,20-dione 17,21-diacetate 9α-chloro-11β, 17α, 21-trihydroxy -16α-methylpregna-1,4-diene-3,20-dione 17-acetate 21-propionate 9α-chloro-11β,17α,21-trihydroxy-16α-methylpregna-1,4-diene-3,20-dione 17-acetate 21-valerate 9α-chloro-11β,17α,21-trihydroxy-16α-methylpregna-1,4-diene-3,20-dione 17-acetate 21-benzoate 9α-chloro-11β,17α,21-trihydroxy-16α-methylpregna-1,4-diene-3,20-dione 17-propionate 21-butyrate 9α-chloro-11β,17α,21-trihydroxy-16α-methylpregna-1,4-diene-3,20-dione 17-propionate 21-valerate 9α-chloro-11β,17α,21-trihydroxy-16α-methylpregna-1,4-diene-3,20-dione 17-propionate 21-benzoate 9α-chloro-11β,17α,21-trihydroxy-16α-methylpregna-1,4-diene-3,20-dione 17,21-dibutyrate 9α-chloro-11β,17α,21-trihydroxy-16α-methylpregna-1,4-diene-3,20-dione 17-butyrate 21-valerate 9α-chloro-11β,17α,21-trihydroxy-16α-methylpregna-1,4-diene-3,20-dione 17-butyrate 21-benzoate 9α-chloro-11β,17α,21-trihydroxy-16α-methylpregna-1,4-diene-3,20-dione 17-valerate 21-propionate 9α-chloro-11β,17α,21-trihydroxy-16α-methylpregna-1,4-diene-3,20-dione 17-valerate 21-butyrate 9α-chloro-11β,17α,21-trihydroxy-16α-methylpregna-1,4-diene-3,20-dione 17,21-divalerate 9α-chloro-11β,17α,21-trihydroxy-16α-methylpregna-1,4-diene-3,20-dione 17-valerate 21-benzoate 9α-fluoro-11β,17α,21-trihydroxy-16α-methylpregna-1,4-diene-3,20-dione 17-propionate 21-butyrate 9α-fluoro-11β,17α,21-trihydroxy-16α-methylpregna-1,4-diene-3,20-dione 17-valerate 21-butyrate.

13. A pharmaceutical composition which contains a compound as claimed in claim 12 together with a pharmaceutical carrier.

14. A pharmaceutical composition according to claim 13 which contains between 0.001 and 0.5% of said compound.

15. A pharmaceutical composition according to claim 14 which contains between 0.01 and 0.25% of said compound.

16. A pharmaceutical composition which contains a compound as claimed in claim 11 together with a pharmaceutical carrier.

17. A compound of the formula

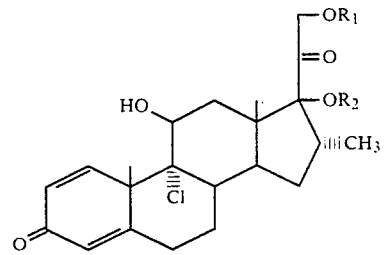

wherein $R_1$ represents an acetyl, propionyl or butyryl group, and $R_2$ is butyryl when $R_1$ is acetyl or propionyl and is acetyl when $R_1$ is butyryl.

18. A compound of claim 17 wherein $R_1$ is propionyl and $R_2$ is butyryl.

19. A compound of claim 17 wherein $R_1$ is acetyl and $R_2$ is butyryl.

20. A compound of claim 17 wherein $R_1$ is butyryl and $R_2$ is acetyl.

21. A pharmaceutical composition a compound of claim 17, together with a pharmaceutical carrier.

22. A pharmaceutical composition which contains an anti-inflammatory amount of a compound of claim 17, together with a pharmaceutical carrier.

23. The pharmaceutical composition according to claim 22 which contains between 0.001 and 0.5% w/w of said compound.

24. The pharmaceutical composition of claim 23 which contains between 0.01 and 0.25% w/w of said compound.

* * * * *

UNITED STATES PATENT AND TRADEMARK OFFICE
CERTIFICATE OF CORRECTION

PATENT NO. : 5,026,693

DATED : June 25, 1991

INVENTOR(S) : Villax et al.

It is certified that error appears in the above-identified patent and that said Letters Patent is hereby corrected as shown below:

Column 4, lines 43 and 45, in both instances, "9α-fluoro-11,17α,21-trihydroxy-16-methylpregna-1,4-" should read --9α-fluoro-11ß,17α,21-trihydroxy-16α-methylpregna-1,4--.

Column 9, line 30, "8" should read --7--, and line 33, "11" should read --1--.

Column 10, line 57, after "composition" insert --which contains--,

Signed and Sealed this

Fifteenth Day of December, 1992

Attest:

DOUGLAS B. COMER

*Attesting Officer*   *Acting Commissioner of Patents and Trademarks*